United States Patent
Broxterman et al.

(10) Patent No.: US 7,371,901 B2
(45) Date of Patent: May 13, 2008

(54) PROCESS FOR THE PREPARATION OF ALKYNOLS

(75) Inventors: Quirinus Bernardus Broxterman, Munstergeleen (NL); Gerardus Karel Maria Verzijl, Well (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/575,757

(22) PCT Filed: Oct. 14, 2004

(86) PCT No.: PCT/EP2004/011614

§ 371 (c)(1),
(2), (4) Date: May 6, 2007

(87) PCT Pub. No.: WO2005/040076

PCT Pub. Date: May 6, 2005

(65) Prior Publication Data

US 2007/0276150 A1    Nov. 29, 2007

(30) Foreign Application Priority Data

Oct. 17, 2003   (EP) ................... 03078277

(51) Int. Cl.
  *C07C 27/10* (2006.01)
  *C07C 29/10* (2006.01)
  *C07C 35/00* (2006.01)
(52) U.S. Cl. .................................... 568/700
(58) Field of Classification Search ............... None
See application file for complete search history.

(56) References Cited

OTHER PUBLICATIONS

Takano et al, Synthesis of Optically Active 4-Benzyloxymethyl- and 4-(4-Methoxyphenoxy)methyl-buten-2-olids via Lipase-Mediated Resolution, Synthesis, No. 12, Dec. 1993, pp. 1253-1256.
Allevi et al, "Lipase-catalysed resolution of (R)- and (S)-1-trimethylsilyl-1-alkyn-3-ols: useful intermediates for the synthesis of opticallhy active gamma-lactones", Tetrahedron, Asymmetry, vol. 8, No. 1, Jan. 9, 1997, pp. 93-99.
Gallagher et al, "PMHS-Mediated Couplings of Alkynes or Benzothiazoles with Various Electrophiles: Application to the Synthesis of (−)-Akolactone", Journal of Organic Chemistry, vol. 68, No. 17, Aug. 22, 2003. pp. 6775-6779.
Thompson et al, "FR901464 Total Synthesis, Proof of Structure, and Evaluation of Synthetic Analogues", Journal of The American Chemical Society, vol. 123, No. 41, Sep. 25, 2001, pp. 9974-9983.
International Search Report mailed Feb. 9, 2005 in PCT/EP2004/011614.

*Primary Examiner*—Yvonne Eyler
*Assistant Examiner*—Kellette Gale
(74) *Attorney, Agent, or Firm*—Nixon & Vanderhye P.C.

(57) ABSTRACT

Process for the preparation of an alkynol with formula $HC\equiv C-CH(OH)-R^2$ (formula 2) wherein $R^2$ represents methyl, halomethyl or ethyl, wherein the corresponding silyl-protected alkynol ester with formula 1

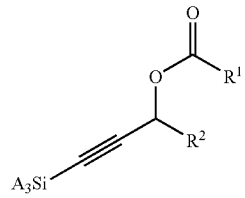

(1)

wherein $R^1$ represents H, or an optionally substituted alkyl, an optionally substituted alkenyl or an optionally substituted (hetero)aryl group, $R^2$ is as defined above and $A_3Si$ represents a trisubstituted silyl group wherein each A independently represents an optionally substituted alkyl or an optionally substituted (hetero)aryl group, in the presence of water and at least an equivalent amount of amine functionalities is converted into the alkynol with formula 2. Preferably, the amount of water is between 0.5 and 3 equivalents calculated with respect to the amount of silyl-protected alkynol ester with formula (1).

11 Claims, No Drawings

PROCESS FOR THE PREPARATION OF ALKYNOLS

This application is the U.S. national phase of international application PCT/EP2004/011614 filed 14 Oct. 2004 which designated the U.S. and claims benefit of EP 03078277.5, dated 17 Oct. 2003, the entire content of which is hereby incorporated by reference.

The invention relates to a process for the preparation of an alkynol with formula HC≡C—CH(OH)—$R^2$(formula 2) wherein $R^2$ represents methyl, halomethyl or ethyl, wherein the corresponding silyl-protected alkynol ester with formula 1

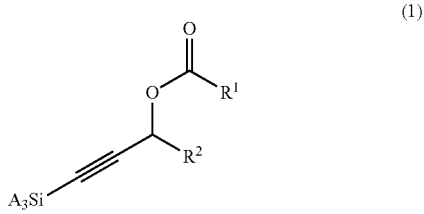

(1)

wherein $R^1$ represents H, an optionally substituted alkyl, an optionally substituted alkenyl or an optionally substituted (hetero)aryl group, $R^2$ is as defined above and $A_3Si$ represents a trisubstituted silyl group wherein each A independently represents an optionally substituted alkyl or an optionally substituted (hetero)aryl group, in the presence of water and at least an equivalent amount of amine functionalities is converted into the alkynol with formula 2. The "at least equivalent amount of amine functionalities" is calculated with respect to the amount of silyl-protected alkynol ester with formula 1.

Deprotection of the silyl-protected alkynol esters with formula 1, wherein both the protecting silyl group and the protecting acyl group are removed are known to be performed, for instance, in methanol in the presence of a base. A disadvantage of this method is that due to equilibrium considerations diluted systems with high amounts of methanol are required. Moreover due to small differences in boiling points between the reaction system and the alkynol with formula 2, isolation via distillation is rather difficult.

Applicant now has developed a simple, one pot deprotection method which can be applied at high concentrations and which leads to virtually quantitative deprotection and high isolated yields of the desired alkynol, and wherein the desired product can easily be separated from the other reaction products.

P. Allevi, et al., Tetrahedron (Asymmetry), 1997, 8(1), 93-99 discloses a process for the preparation of 1-benzyloxy-3-butyn-2-ol and 1-(4-methoxyphenoxy)-but-3-yn-2re-spectively by the concurrent deacylation and desilylation of 3-acetoxy-1-trimethylsilyl-1-undecyne, the process being carried out in methanolic potassium carbonate.

W. P. Gallagher, et al., Journal of Organic Chemistry, 2003, 68(17), 6775-6779 discloses a process for the desilylation of (R)-4-trimethylsilyl-3-butyn-2-ol by using tetrabutylammonium fluoride (TBAF).

The deprotection according to the invention is performed in the presence of water and an equivalent amount of amine functionalities. The amount of water in the process of the present invention preferably is at least 0.1 equivalents calculated with respect to the amount of silyl-protected alkynol ester with formula 1 to be deprotected, more preferred at least 0.2 equivalents, even more preferred at least 0.3 equivalents, particularly preferred at least 0.4 equivalents and most preferred at least 0.5 equivalents of water. If distillation forms (part of) the purification process (to which the reaction mixture after the deprotection process may be subjected), the amount of water preferably is less than 5 equivalents, more preferred less than 4 equivalents, particularly preferred less than 3 equivalents, most preferably less than 2 equivalents. In this case large amounts of water are disadvantageous in that they have to be removed before distillation of the alkynol with formula 2. Moreover if water forms an azeotrope with the alkynol with formula 2, water has to be removed by drying or any other physical or chemical method that is compatible with the system. Preferably less than 3, more preferably less than 1 equivalent of water calculated with respect to the amount of silyl-protected alkynol ester with formula 1, is used in the deprotection step. Particularly advantageous is the use of 0.4-0.6 equivalents of water relative to the amount of silyl-protected alkynol ester with formula 1.

In order to introduce the amine functionalities in the process of the present invention, primary or secondary amines may be used. Suitable primary or secondary amines that can be used in the process of the present invention are, for instance, amines with 1-40 C atoms, including of course also for instance diamines and polyamines etc., amino alcohols, including any compound with one or more, for instance 1-20 (primary or secondary) amino groups and one or more, for instance 1-20 hydroxy groups, for instance amino alcohols having one amino group and one hydroxy group, in particular aminoethanol; amino diols, for instance diethanol amine; amino polyols; diamino glycols; polyamino polyols; aminothiols, including any compound with one or more, for instance 1-20 (primary or secondary) amino groups and one or more, for instance 1-20 SH groups, for instance amino thiols having one amino group and one SH group; amino thiols, for instance cysteine and derivatives thereof, amino poly thiols or polyamino polythiols. Accordingly, one molecule of the primary or secondary amine can contain more than 1 equivalent of amine functionalities. Preferably a primary amine or an amino alcohol, more preferably an aminodiol, particularly diethanolamine is used.

The amount of primary or secondary amine to be used may vary within wide limits. Preferably, less than 5 equivalents of the amine compound are used with respect to the amount of silyl-protected alkynol ester with formula 1, more preferably less than 2 equivalents, and most preferably the amine is used in an amount between 1 and 2 equivalents with respect to the alkynol ester of formula 1. Based on the amount of amine functionalities, preferably less then 100 equivalents of amine functionalities are used calculated with respect to the amount of silyl-protected alkynol ester with formula 1, more preferably less than 50 equivalents, even more preferred, less than 20 equivalents of amine functionalities, particularly preferred less than 10 equivalents and most preferred between 1 and 5 equivalents of amine functionalities compared to alkynol ester of formula 1.

The deprotection method according to the invention preferably is catalyzed by an amount of a base. Suitable bases that can be used are, for instance, (earth) alkali metal (bi)carbonates, (earth) alkali metal hydroxides, (earth) alkali metal alkoxides and (earth) alkali metal phenoxides. The term "(earth) alkali metal" is used to define both alkali metals and earth alkali metals. Preferably an (earth) alkali metal carbonate, bicarbonate or hydroxide is used as the base. The basic functionality of the primary or secondary amine can of course also be applied as the base. The amount of base to be used may range within wide limits and may vary from catalytic amounts, for instance ≧0.01 equivalents calculated with respect to the amount of silyl-protected alkynol ester of formula 1, up to 5, preferably up to 2 equivalents in a non-catalytic mode. In case distillation forms part of the purification, the preferred amount of base may depend on the boiling point of the base. If the difference in boiling points of the base and the alkynol with formula 2 is smaller than 45° C., preferably a catalytic amount of base, for instance 0.01-0.1 equivalents, is used.

The temperature at which the deprotection is performed is not critical and lies for instance between −10 and 150° C., preferably between 10 and 100° C., most preferably between 30 and 80° C.

The deprotection according to the invention may if desired be performed in the presence of a solvent in order to enhance the solubility of the various reacting agents. If no solvent is used in the deprotection, preferably the reagents are chosen such that the reaction system is as homogeneous as possible. Preferably no solvent is used as the process appears to be most efficient without the use of a solvent. Suitable solvents that may be used are for instance inert solvents having a high boiling point, for instance a boiling point of 200° C. or more, for example dibenzylether.

After the deprotection step the reaction mixture, which may be homogeneous or may consist of two or more phases, may be subjected to purification. The purification may consist of one or more steps, preferably at least one of these steps is a distillation step. Before or after the distillation of the alkynol with formula 2, the purification may comprise for instance one or more extractions, filtrations, phase separations or distillations, if any.

In a particularly advantageous embodiment of the process according to the invention wherein purification is (partly) achieved by a distillation step, the reaction components are chosen such that the reagents present in the mixture subjected to distillation—optionally after one or more purification steps—have a boiling point which differs at least 45° C., preferably at least 55° C., from the boiling point of the alkynol with formula 2; alternatively, if the said boiling point difference is lower, preferably less than stoichiometric amounts (for example, ≦10 mol % compared to the amount of alkynol with formula 2) are present in the medium to be distilled. Preferably the phase containing the alkynol with formula 2 which is subjected to distillation contains the lowest possible amount of compounds having a boiling point which differs less than 45° C. from the boiling point of the alkynol with formula 2 and/or contains the lowest possible amount of water. Preferably this amount of water is less than 3 equivalents calculated with respect to the amount of alkynol with formula 2.

The phase containing the alkynol with formula 2 which is subjected to distillation, preferably contains less than 10 mol % calculated with respect to the amount of alkynol with formula 2, of each component of which the difference in boiling point compared to the boiling point of the alkynol with formula 2 is less than 45° C.

The deprotection according to the invention can be performed starting from any silyl-protected alkynol ester of formula 1 wherein $R^1$ represents H, an optionally substituted alkyl group with for instance 1-20 C-atoms, preferably 1-6 C-atoms, an optionally substituted alkenyl group with for instance 2-20 C-atoms, preferably 2-6 C-atoms, or an optionally substituted (hetero)aryl group optionally containing one or more O or N atoms, with for instance 4-20 C-atoms, preferably 5-10 C-atoms; $A_3Si$ represents a trisubstituted silyl group wherein each A independently represents an optionally substituted alkyl group with for instance 1-20 C-atoms or an optionally substituted (hetero)aryl group, for instance a phenyl group; and wherein $R^2$ represents methyl, halomethyl, wherein halo represents F, Cl, Br or I, preferably Cl, or ethyl. The alkyl, alkenyl and (hetero)aryl groups of $R^1$ or A may contain any substituents/functional groups that are inert in the reaction system. Suitable substituents are, for example, alkyl groups, (hetero)aryl groups, alkoxy groups, alkenyl groups, dialkylamino groups, trialkylamino groups (resulting in $R^1$ being a tetrasubstituted ammonium salt), halogens, nitrile, nitro, acyl, carboxylic, carbonyl, carbamoyl or sulphonate groups which may contain for instance 0-10 C-atoms. A preferred alkynol ester of formula 1 is one for which $R^1$ is a carboxylic substituted alkyl group, such as, for example —$(CH_2)_2$—COOH (mono succinic ester). Another preferred alkynol ester of formula 1 is one for which $R^1$ is a tetra-alkyl ammonium salt ($R^1$ is an alkyl group substituted with a trialkylamino group).

The (protected) alkynols may be in an enantiomerically enriched form, for instance with an ee>80%, preferably an ee>90%, most preferably an ee>95%, in particular an ee>99%.

In case the silyl-protected alkynol ester with formula 1 is in enantiomerically enriched form, this enantiomerically enriched silyl-protected alkynol ester may first be prepared via enzymatic resolution of a mixture of enantiomers of the corresponding silyl-protected alkynol of formula 7

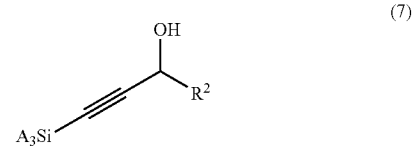

(7)

followed by isolation of the enantiomerically enriched silyl-protected alkynol ester with formula 1. The isolation of the enantiomerically enriched silyl-protected alkynol ester with formula 1 may for example take place by separation of the (R)-alkynol ester with formula 1 or the (S)-alkynol ester with formula 1 from respectively the (S)-alkynol or (R)-alkynol with formula 7 in the reaction mixture. This can, for instance, be achieved by converting the remaining (S)- or (R)-alkynol of formula 7 to a high boiling or water soluble compound. Preferably, the remaining (S)- or (R)-alkynol of formula 7 is converted to a high boiling or water soluble ester with a suitable acylating agent and optionally a suitable catalyst. The configuration of the prepared alkynol ester of formula 1 or the remaining silyl-protected alkynol of formula 7 depends on the enantioselectivity of the enzyme used in the enzymatic resolution process.

An alkynol with formula 2 that particularly advantageously can be prepared with the process according to the invention is 3-butyn-2-ol or its enantiomers, in particular (R)- or (S)-3-butyn-2-ol starting from an ester of (R)- or (S)-4-trialkylsilyl-3-butyn-2-ol, for instance an ester of (R)- or (S)-4-trialkylsilyl-3-butyn-2-ol and a carboxylic acid or a mono ester of (R)- or (S)-4-trialkylsilyl-3-butyn-2-ol and succinic acid.

The starting material of the deprotection process, for example the ester of (R)- or (S)-4-trialkylsilyl-3-butyn-2-ol, may, for instance, be prepared via (enzymatic) resolution, for instance by (enzymatic) stereoselective acylation, wherein a mixture of (S)- respectively (R)-4-trialkylsilyl-3-butyn-2-ol and the ester of (R)-respectively (S)-4-trialkylsilyl-3-butyn-2-ol is obtained, followed by separation of the (R)- respectively (S)-4-trialkylsilyl-3-butyn-2-ol ester and the (S)- respectively (R)-4-trialkylsilyl-3-butyn-2-ol in the mixture, for instance by converting (S)- respectively (R)-4-trialkylsilyl-3-butyn-2-ol to a high boiling or water soluble ester, for instance a succinic ester, with a suitable acylating agent, for instance succinic anhydride, and a suitable catalyst, for instance dimethylamino pyridine.

The invention will further be elucidated by the following examples, without however be restricted thereby.

Deprotection Trialkylsilyl Esters

Deprotection examples according to the scheme below are illustrated in the examples for compound 1a.

Scheme

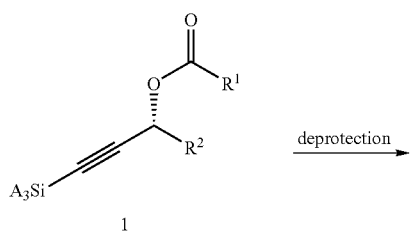

1
1a A = $R^1$ = $R^2$ = Me
1a' A = $R^2$ = Me, $R^1$ = —($CH_2$)$_2$COOH

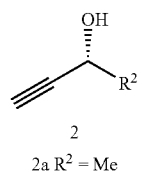

2
2a $R^2$ = Me

As is clear from the above scheme and illustrated in the examples for compound 1a, compound 1a respectively compound 1a' can be converted into compound 2a with the process of the present invention.

The deprotection reaction and side products are monitored by GC-analysis using a CP-Sil 5 CB column (program: 3 minutes at 50° C., 15° C./min→250° C., 5 minutes at 250° C.)

Side Products

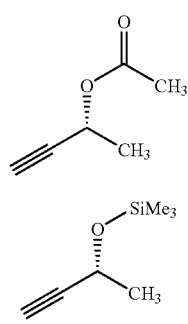

3a

4a

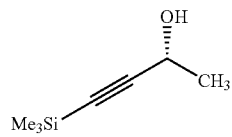

5a

EXAMPLE I

Deprotection Using n-butylamine

A 5 ml vial containing a magnetic stirring bar was charged with (R)-4-trimethylsilyl-3-butyn-2-yl acetate (1a) (1 mmol), $K_2CO_3$ (0,1 mmol) and n-butylamine (2.4 mmol). Reaction vial was sealed with a teflon-lined cap and the temperature of the reaction mixture was increased to 80° C. After 3 hours, water (1.2 mmol) was added to the reaction mixture. Reaction was continued for 1 night giving 2a in 97% yield. Starting material 1a was not completely converted. Starting material 1a and side product 5a stayed behind in the reaction mixture in respectively 1 and 3% assay yield.

EXAMPLE II

Deprotection Using Amino Alcohols

A 5 ml vial containing a magnetic stirring bar was charged with (R)-4 -trimethylsilyl-3-butyn-2-yl acetate (1a) (1 mmol), $K_2CO_3$ (0, 1 mmol) and amino alcohol. Reaction vial was sealed with a teflon-lined cap and the temperature of the reaction mixture was increased to 80° C. At given reaction time (table 1), water was introduced in the reaction mixture. Reaction was continued overnight at 80° C. Deprotection results are summarized in table 1.

TABLE 1

Deprotection of 1a using amino alcohols

| Exp | Amino alcohol | (eq.) | $H_2O$ (mmol) | t (h)[a] | 2a | 3a | 4a | 5a | 1a |
|---|---|---|---|---|---|---|---|---|---|
| 1 | 2-amino-1-butanol | 1.2 | 1.2 | 3 | >99 | | | <1 | |
| 2 | Diethanolamine | 1.2 | 0.6 | 0 | 99 | | | 1 | |
| 3 | Diethanolamine | 1.2 | 1.6 | 0 | 98 | | | 2 | |
| 4 | Diethanolamine | 1.2 | 1.2 | 3 | >99 | | | | |
| 5 | Diethanolamine | 1.2 | 0.6 | 4 | >99 | | | | |

Yield[b] (%)

[a]reaction time before the addition of water
[b]determined by GC using the "corrected 100% method"

EXAMPLE III

Deprotection (R)-4-trimethylsilyl-3-butyn-2-yl acetate (1a) and Isolation of (R)-3-butyn-2-ol by Distillation

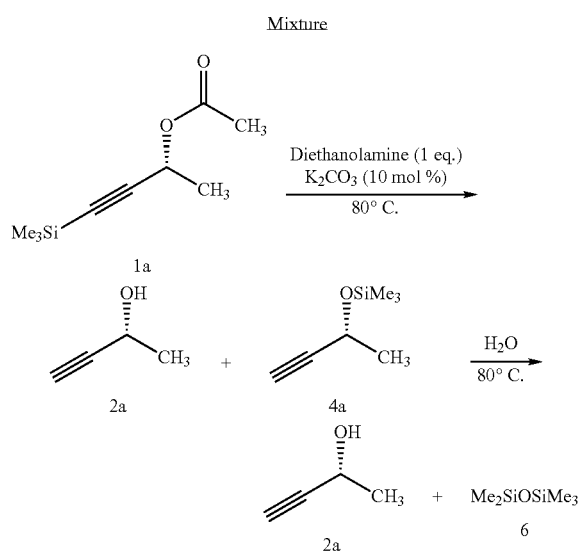

A 500 ml round bottom flask was charged with (R)-4-trimethylsilyl-3-butyn-2-yl acetate (1a) (68.41 g, ~0.37 mol), diethanolamine (41.0 g, 0.39 mol) and $K_2CO_3$ (5.1 g, 0.037 mol). The reaction mixture was stirred at 80° C. for 1.5 hours. In first part of the deprotection, (R)-4-trimethylsilyl-3-butyn-2-yl acetate was completely converted to a mixture of (R)-3-butyn-2-ol and (R)—O-TMS-butynol (4a). In second part, the remaining (R)—O-TMS-butynol (4a) was converted to (R)-3-butyn-2-ol by the addition of $H_2O$ (4 g, 0.22 mol). The reaction was continued for 2 h at 80° C. in order to achieve complete conversion.

Upon standing, the reaction mixture separated into two liquid layers. One layer is predominantly TMS-ether 6 and second layer exists of a solution of (R)-3-butyn-2-ol in the remaining reaction matrix.

Distillation

The two-phase reaction mixture was distilled directly after deprotection by slow increase of temperature to 120° C. In first fraction, an azeotropic mixture of TMS-ether 6 and (R)-3-butyn-2-ol (2a) came over, which separated in the receiver into two liquid layers. At this point, (R)-3-butyn-2-ol (2a) was separated in high purity from TMS-ether 6. Distillation of the remaining (R)-3-butyn-2-ol was continued at 120° C. by slow decrease of the pressure to approximately 800 mbar. When distillation was almost finished the pressure was further decreased in order to distill residual amounts of (R)-3-butyn-2-ol. The combined distillation fractions (product separated from 6 in first fraction and product collected in second fraction) yielded 24.1 g (0.34 mol) (R)-3-butyn-2-ol.

For further purification, the collected (R)-3-butyn-2-ol fractions were distilled at atmospheric pressure at an oil bath temperature of 125° C. (R)-3-butyn-2-ol (18.0 g, 0.26 mol) was smoothly distilled at a bottom temperature of 108-110° C. Quantitative analysis by GC using an external standard method showed a high degree of purity.

EXAMPLE IV

Deprotection Using 1,2-diaminoethane

A 5 ml vial containing a magnetic stirring bar was charged with (R)-4-trimethylsilyl-3-butyn-2-yl acetate (1a) (1 mmol), dihexylether as internal standard (0.1 mmol), $H_2O$, $K_2CO_3$ and 1,2-diaminoethane (1.2 mmol). Reaction vial was sealed with a teflon-lined cap and the temperature of the reaction mixture was increased to 80° C. Deprotection was continued for 16 h at given temperature.

For analysis, reaction mixture was diluted with 1 ml dichloromethane. GC-sample was prepared by dissolving 50 μl of vigorous stirring reaction mixture in 1 ml $CH_2Cl_2$. The results are summarized in table 4

TABLE 4

| Deprotection 1a using 1,2-diaminoethane | | | | | | | |
|---|---|---|---|---|---|---|---|
| | $K_2CO_3$ | $H_2O$ | Yield[a] (%) | | | | |
| Exp | (mmol) | (mmol) | 2a | 3a | 4a | 5a | 1a |
| 1[b] | | | 33 | | 2 | 53 | 12 |
| 2 | | 1.6 | 99 | | 1 | | |
| 3 | 0.1 | 1.6 | 100 | | | | |

[a]Assay yield determined by GC using dihexyl ether as internal standard
[b]Comparative experiment

The invention claimed is:

1. Process for the preparation of an alkynol with formula HC≡C—CH(OH)—$R^2$ (formula 2) wherein $R^2$ represents methyl, halomethyl or ethyl, wherein the corresponding silyl-protected alkynol ester with formula 1

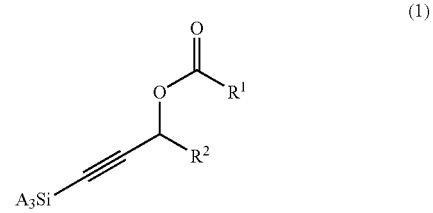

(1)

wherein $R^1$ represents H, an optionally substituted alkyl, an optionally substituted alkenyl or an optionally substituted (hetero)aryl group, $R^2$ is as defined above and $A_3Si$ represents a trisubstituted silyl group wherein each A independently represents an optionally substituted alkyl or an optionally substituted (hetero)aryl group, in the presence of water and at least an equivalent amount of amine functionalities is converted into the alkynol with formula 2.

2. Process according to claim 1 wherein the amount of water is between 0.5 and 3 equivalents calculated with respect to the amount of silyl-protected alkynol ester with formula 1.

3. Process according to claim 1 wherein in addition a base is present.

4. Process according to claim 3, wherein the base is an (earth) alkali metal carbonate, an (earth) alkali metal bicarbonate or an (earth) alkali metal hydroxide.

5. Process according to claim 1,
wherein the amount of amine is between 1 and 2 amine equivalents calculated with respect to the amount of silyl-protected alkynol ester with formula 1.

6. Process according to claim 1, wherein $R^2$=methyl.

7. Process according to claim 1, wherein subsequently the reaction mixture is subjected to at least one purification step of which at least one step is a distillation step.

8. Process according to claim 7, wherein the phase containing the alkynol with formula 2 which is subjected to distillation (i) contains less than 3 equivalents calculated with respect to the amount of alkynol with formula 2 of water and (ii) contains less than 10 mol % calculated with respect to the amount of alkynol with formula 2, of each component of which the difference in boiling point compared to the boiling point of the alkynol with formula 2 is less than 45° C.

9. Process according to claim 1, wherein the silyl-protected alkynol ester with formula 1 is enantiomerically enriched.

10. Process according to claim 9, wherein first the enantiomerically enriched silyl-protected alkynol ester with formula 1 is prepared via enzymatic resolution of the mixture of enantiomers of the corresponding silyl-protected alkynol with formula 7,

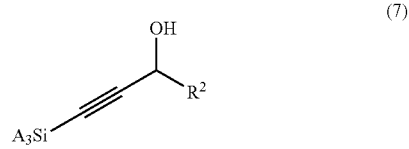

followed by isolation of the enantiomerically enriched silyl-protected alkynol ester with formula 1.

11. Process according to claim 10, wherein the enzymatic resolution is performed via stereoselective acylation followed by conversion of the remaining enantiomerically enriched enantiomer of the silyl-protected alkynol ester with formula 1 to a high boiling or water soluble compound.

* * * * *